US00PP15851P2

(12) United States Plant Patent
McLaren

(10) Patent No.: US PP15,851 P2
(45) Date of Patent: Jul. 12, 2005

(54) APRICOT TREE, 'F160 CV'

(50) Latin Name: *Prunus armeniaca*
Varietal Denomination: F160 cv

(75) Inventor: John McLaren, Cromwell (NZ)

(73) Assignee: Nevis Fruit Company USA LLC, Boulder, CO (US)

( * ) Notice: Subject to any disclaimer, the term of this patent is extended or adjusted under 35 U.S.C. 154(b) by 49 days.

(21) Appl. No.: 10/846,121

(22) Filed: May 14, 2004

(51) Int. Cl.[7] ..... A01H 5/00
(52) U.S. Cl. ..... Plt./186
(58) Field of Search ..... Plt./186

*Primary Examiner*—Anne Marie Grunberg
(74) *Attorney, Agent, or Firm*—Wells St. John P.S.

(57) ABSTRACT

A new and distinct variety of apricot tree is disclosed and which is mature for harvesting and shipment under the ecological conditions prevailing in Eastern Washington, about August 11$^{th}$ to August 14$^{th}$.

3 Drawing Sheets

BACKGROUND OF THE NEW VARIETY

The present invention relates to a new and distinct variety of apricot tree, (*Prunus armeniaca* L) and which has been denominated varietally as 'F160cv' hereinafter, and more specifically to a new apricot tree variety which is characterized as to novelty by bearing large, light orange-colored fruit having some pinkish red blush and which is mature for harvesting and shipment from about August 11$^{th}$ to about August 14$^{th}$ under the ecological conditions prevailing in Orondo, Wash.

ASEXUAL REPRODUCTION

The present variety of apricot tree was originated by me from a cross which I conducted between the unpatented apricot varieties "Sundrop" with a late "Moorpark" selection in 1987. This cross took place at my orchard which is located in Central Otago, New Zealand. The present variety of apricot tree showed promising characteristics and was selected in 1992 for further asexual propagation. Thereafter, budwood was removed from the same tree and was grafted into other test trees growing in the same orchard. Since the identification of this new variety in 1992, these further asexual reproductions have been continually observed, and other budwood has been grafted into various rootstocks such as peach, apricot and plum. These subsequent test trees have all been observed, and the trees and fruit produced by these same asexual reproductions appear to be true to the original parent tree. In 1995, budwood of the present variety of apricot tree was sent to the quarantine facility, IR-2, at Prosser, Wash. for further virus testing. Subsequently, virus-free material was released in 1997, and test trees were grafted and subsequently planted in a test orchard which is located near Orondo, Wash. in 1999. The inventor, and his representatives have continued to observe these test trees, and have confirmed that the characteristics of these test trees remain true to the original parent tree. In comparison to 'Sundrop', the present variety is ready for harvesting 53 days later and in comparison to 'Moorpark', the present variety ripens 31 days later under conditions existing in New Zealand.

SUMMARY OF THE VARIETY

The new variety of apricot tree, 'F160 cv' is characterized as to novelty, and is otherwise deemed noteworthy by producing fruit which ripen in the late season, and which is mature for harvesting and shipment at least five weeks later than the "Perfection" apricot variety (unpatented) under the environmental conditions prevailing in Orondo, Wash.

BRIEF DESCRIPTION OF THE DRAWINGS

The accompanying drawings are color photographs of various aspects of the present plant. The colors are as nearly true as is reasonably possible in color representations of this type. Due to chemical development, processing and printing, the leaves and fruit of the present tree may, or may not be, accurate when compared to the actual specimen. For this reason, future color references should be made to the color plates as provided by the Munsell Book of Color, and the other general color descriptions as provided for hereinafter.

DETAILED DESCRIPTION

Figure 1:
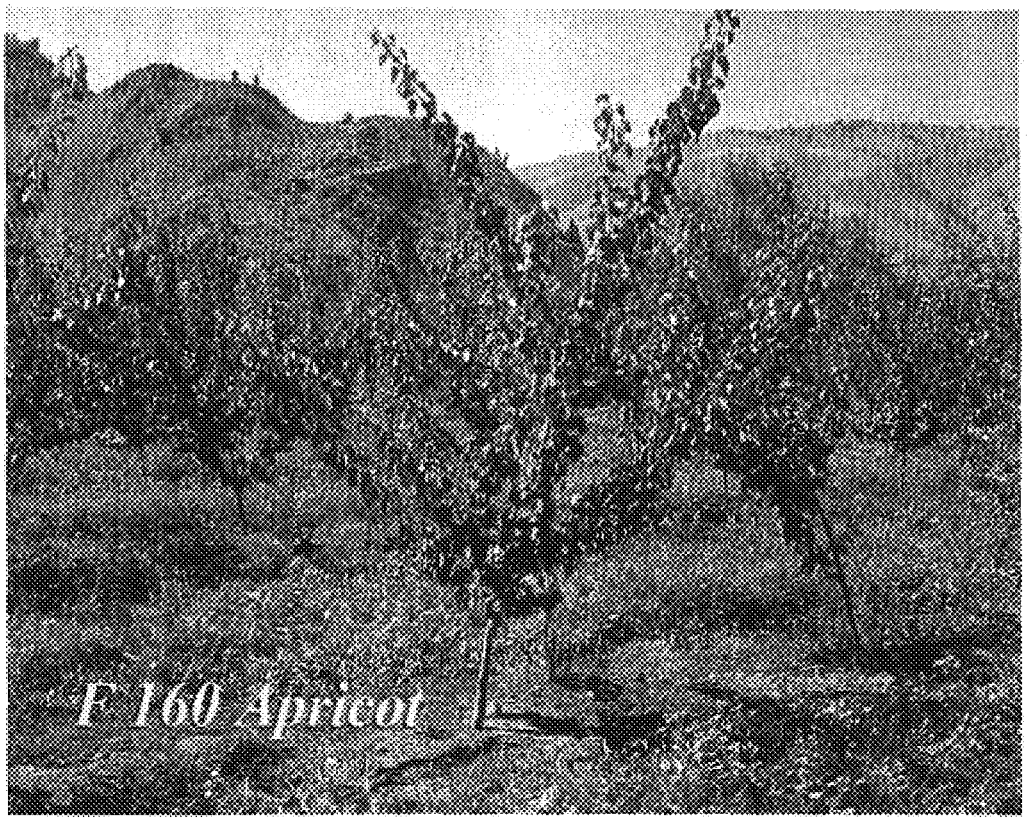
FIG. 1 shows the growing habit of second generation trees of the new variety of apricot tree as presently growing at a test orchard in Orondo, Wash. during August of 2003.
Figure 2:
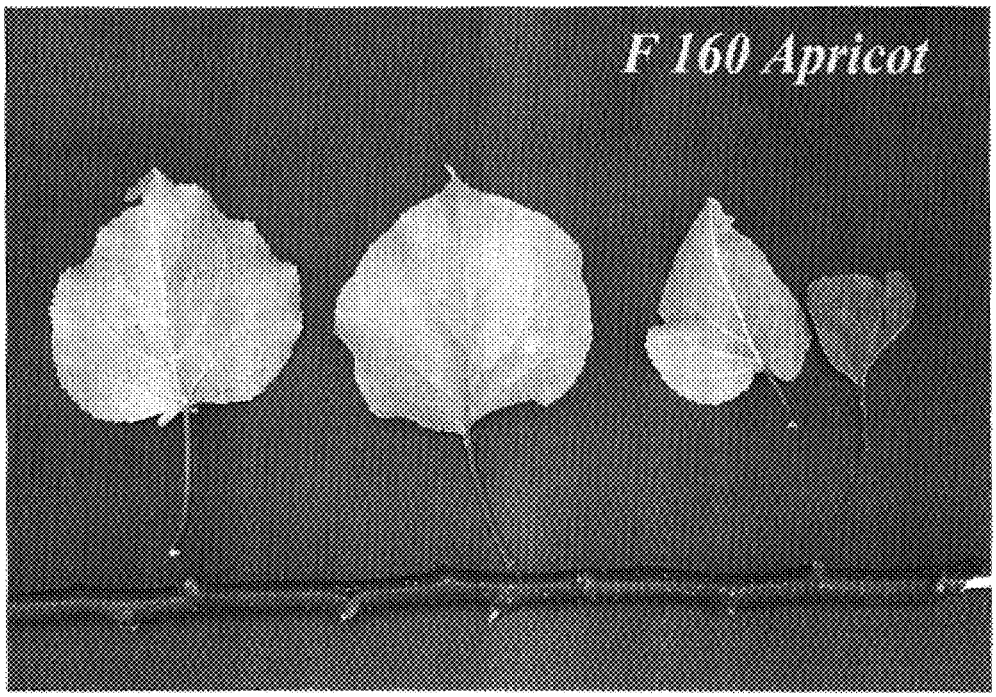
FIG. 2 shows the dorsal and ventral surfaces as well as the new wood characteristics of mature leaves, (left) and immature leaves, (right) of the new variety of apricot tree.
Figure 3:
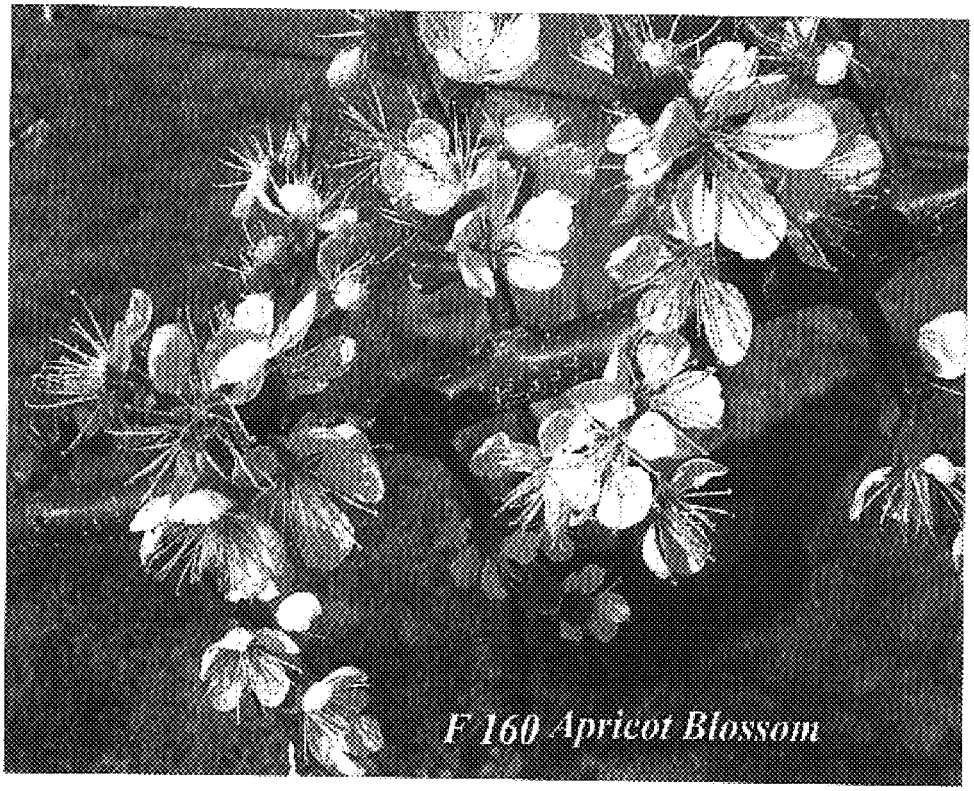
FIG. 3 shows the blossom characteristics of the present variety of apricot tree in full bloom and as seen on Mar. 22, 2003.
Figure 4:
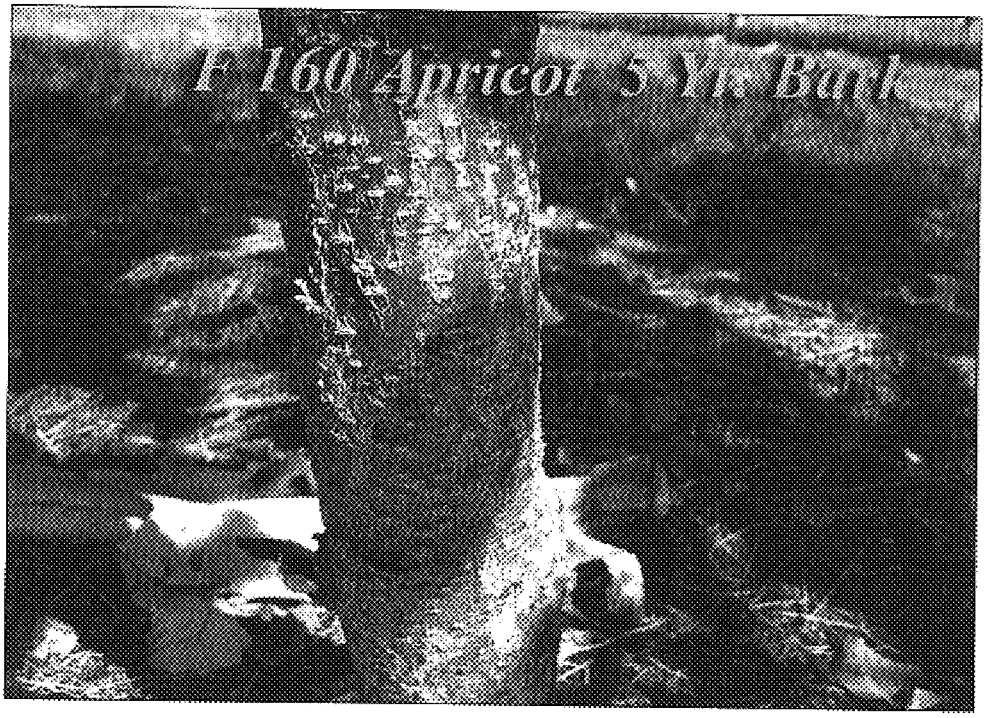
FIG. 4 illustrates the characteristics of 5 year old bark currently growing on a test tree.

Referring more specifically to the pomological details of this new and distinct variety of apricot tree, the following has been observed during the 2003 growing season under the ecological conditions prevailing in an orchard located near Orondo, Wash. All major color code designations are by reference to the Munsell Book of Color. Common color names are also used occasionally.

TREE

Tree size: Considered average. Fourth leaf trees (four years in the field) have a height of about 3 to about 4 meters; and a width of about 2 to about 3 meters.

Productivity: Considered average. About 3 to about 4 kg. of fruit per tree were harvested in their fourth leaf.

Vigor: Considered vigorous. The present variety shows about 1 to about 1.5 meters of annual growth. All test trees are presently grafted onto "Manchurian" (unpatented) apricot rootstock.

Growing habit: Considered spreading.

Chilling requirement: The chilling requirements of the present variety of apricot tree appears to be similar to other common commercial apricot varieties, based upon the observations of these same trees as grown in New Zealand; and in the state of Washington. Actual chilling requirements have not been determined but do not appear to be distinctive of the present variety.

Regularity of bearing: Considered regular and uniform.

TRUNK

Size: Considered average for this variety. The present tree was about 5 cm. in diameter when measured at a distance of about 0.3 meters from the surface of the ground.

Bark color: Considered a medium brown (5 YR 4/4).

Lenticels: Density — Considered average, approximately 3 lenticels per square cm.

Lenticels: Shape — Elongated, and having a length of about 3 mm. and a width of about 1 mm.

Lenticels: Color — Light tan (5 YR 8/2).

BRANCHES

Growth habit: Vigorous and spreading, and commonly having an annual growth of 1 to about 2 meters.

Surface texture: One year wood has a substantially smooth surface texture which becomes increasingly rough as the wood ages.

Bark color: Reddish to reddish brown (2.5 YR 3/4) and becoming a darker brown (7.5 YR 4/4) at the base of the shoot.

Pubescence: Not observed.

Lenticels: Numbers — Approximately 15 lenticels per square cm. The lenticels are small and round, and have a dimension of less than about 0.5 mm.

Lenticels: Color — Tan (10 YR 7/4).

Internodes: Length — About 1.5 to about 2 cm. on current season shoot.

LEAVES

Leaf size: Considered medium to large. The leaves are variable in length and width, from about 4.5 to about 8.5 cm. in length; and about 5.5 to about 8 cm. in width.

Leaf form: Generally considered to be a typical apricot leaf. In this regard, the leaf appears somewhat rounded, and having a lanceolate tip and an obtuse base. The base appears to be oriented at substantially about 90 degrees relative to the leaf petiole.

Leaf form: Upper Surface — The leaves tend to roll inwardly at the edges. The upper surface also has a somewhat wavy appearance.

Leaf color: Dorsal Surface — medium green (5 GY 6/6).

Leaf color: Ventral Surface — light grey-green (5 GY 6/6).

Leaf color: Mid vein — Considered reddish purple (2.5 R 3/10).

Marginal form: Considered finely to coarsely serrate. About 6 serrations appear per cm.

Mid-vein thickness: About 1.5 mm.

Leaf glandular characteristics: As a general matter, up to 3 leaf glands which have a length dimension of approximately 1 mm. appear near the base of the leaf blade on the upper surface of petiole. This appears to be unique and characteristic for this particular variety of apricot tree, and is not seen in other common apricot varieties such as the "Perfection" (unpatented) apricot tree.

Stipules: Not observed.

Leaf petiole: Size — Considered average, about 3 to 4 cm. in length; and about 1 to about 2 mm. in diameter.

Leaf petiole: Color — Considered reddish purple (2.5 R 3/10).

FLOWER

Time of bloom: Date of full bloom was observed on Mar. 22, 2003 under the ecological conditions prevailing near Orondo, Wash. First Bloom was observed on Mar. 18, 2003. Petal fall was observed on Mar. 27, 2003.

Flower buds: Size — Generally speaking, dormant flower buds have a length dimension of about 3.5 mm, and a width dimension of about 1.5 mm.

Dormant flower buds: Surface Texture — Considered glabrous.

Dormant flower buds: Color — Dormant flower buds have a brown color (2.5 YR 2/4).

Size of flower: On average, the flower is about 20 to 30 mm in diameter at full bloom.

Flower petals: Length — About 15 mm.

Flower petals: Width — About 10 mm.

Flower petals: Color — At the popcorn stage the flower petals are light pink (2.5 R 9/2). The petals are completely white in color when the flower is in full bloom.

Sepals: Color — Bright red (5 R 4/14).

Stamens: Numbers — About 14 to about 20 are found per flower.

Stamens: Length — About 8 to about 12 mm.

Anthers: Color — Yellow (5 Y 5/12).

Pistil: Length — About 15 mm.

Stigma: Length — About 1.5 mm.

Bloom fragrance: None is apparent.

FRUIT

Maturity when described: Generally, the fruit produced by the present variety of apricot tree is described as it will be found at full commercial maturity. In this regard, the fruit of the present variety was ripe for commercial harvesting and shipment under the ecological conditions prevailing near Orondo, Wash. on Aug. $11^{th}$ to about Aug. $14^{th}$ 2003. This harvesting date is considered to be at least 21 to 28 days later than the apricot tree "Perfection", and about 14 days later than the apricot tree "Tilton" (unpatented) when grown at the same geographical location.

Fruit size: Considered medium to large for the species. On average, the typical fruit is about 50–60 mm in diameter. The average weight of the fruit is about 74 grams.

Fruit form: Considered globose and symmetrical.

Suture: Present, and considered shallow.

Stem cavity: Depth — About 5 mm.

Stem cavity: Width — About 15 mm.

Stem: Length — About 2 mm.

Stem: Thickness — About 2 mm.

Skin thickness: Generally — Considered thin and very tender.

Skin texture: As a general matter it is considered to be tender, melting, smooth and non-glossy.
Blush color: Occasionally, an orange-red blush appears (7.5 R 5/14).
Ground color: Yellow-orange (7.5 YR 8/10).
Tendency to crack: Not observed.
Flesh color: Considered a bright orange (7.5 YR 7/16).
Pubescence: A light pubescence may be found over the entire fruit surface.
Juice production: Considered very juicy.
Flesh flavor: Considered sweet to sub-acid.
Soluble solids: About 18% when fully ripe. The flavor is considered excellent.
Aroma: Not distinctive.
Flesh texture: Variable from average to soft.
Fibers: Not observed.
Ripening characteristics: Uneven. The present variety tends to ripen sooner at the apex.
Eating quality: Considered excellent, and superior to the fruit produced by the "Perfection" apricot tree (unpatented); and the "Tilton" variety of apricot tree which has a much milder flavor.

STONE

Figure 5:
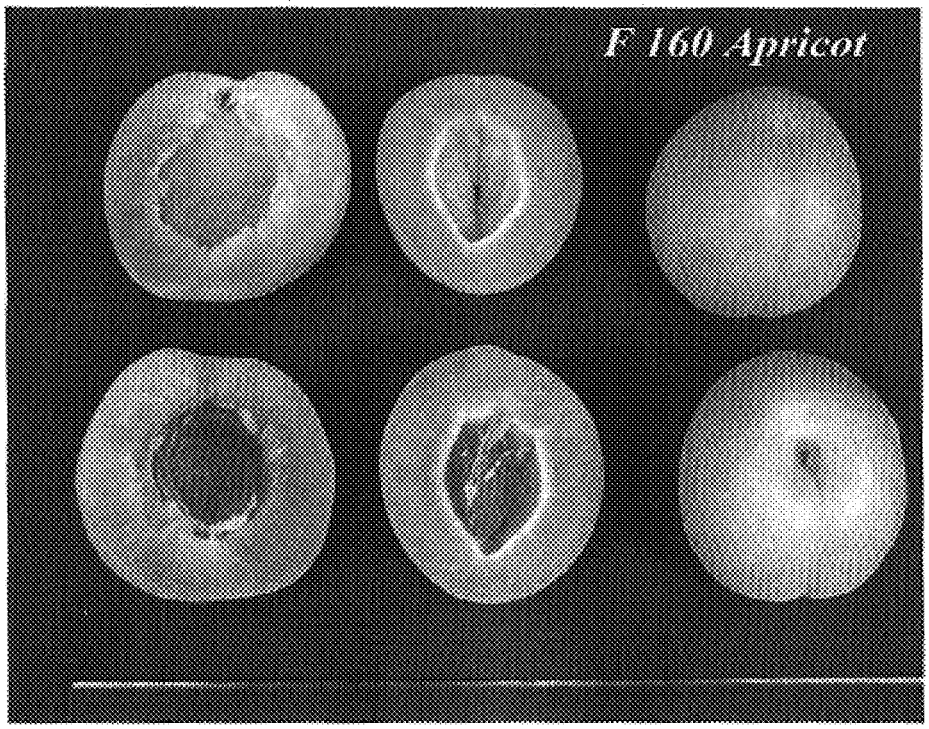
FIG. 5 illustrates several mature fruit of the present variety, two of which have been dissected in the longitudinal and transverse planes, and which shows the flesh and stone characteristics thereof.
Figure 6:
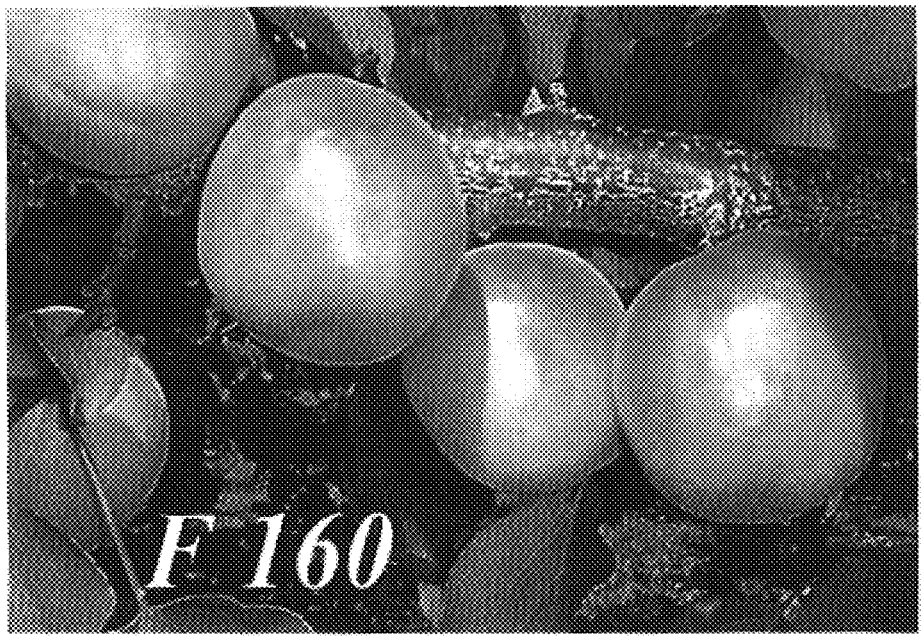
FIG. 6 illustrates the fruit of the present variety of apricot tree at a stage of development where it is sufficiently matured for harvesting and shipment.

Attachment: Considered freestone. The only attachment appears to be at the base of the stone, and no noticeable fibers are present. This is seen most clearly by reference to FIG. 5.
Stone size: Considered medium to large.
Stone length: About 25 mm.
Stone width: About 21 mm.
Stone thickness: About 13 mm.
Stone form: Ovoid.
Stone: Base — Considered acute.
Apex-shape: Considered blunt and rounded.
Stone side-shape: Generally considered equal.
Ridges-form: Three relatively sharp ridges are normally found.
Stone surface texture: Irregular, and considered slightly pebbled in appearance.
Stone color: (Dry) Tan with an orange tint (7.5 YR 6/6).
Pit color: Light tan (7.5 YR 7/6).
Pit-form: Plump, and having a bitter taste. The pit further has a hard shell.
Intended use: The present variety of apricot tree produces fruit which appear to be useful for the commercial fresh market.
Disease and insect resistance: No specific susceptibilities were noted.
Keeping quality: Considered excellent. The fruit of the present variety was kept in cold storage for 2–4 weeks at 2 degrees C. with no deleterious effects noted.

Although the new variety of apricot tree possesses the described characteristics as a result of the growing conditions prevailing in Eastern Washington, it is to be understood that variations in the usual magnitude and characteristics incident to growing conditions, fertilization, pruning and pest control are to be expected.

Having thus described and illustrated my new variety of apricot tree, what I claim is new and desire to secure by Plant Letters Patent is:

1. A new and distinct variety of apricot tree, substantially as illustrated and described, and which produces fruit which are mature for harvesting and shipment about Aug. $11^{th}$ to the $14^{th}$ under the ecological conditions prevailing in Eastern Washington.

* * * * *